United States Patent [19]
West

[11] Patent Number: 5,908,384
[45] Date of Patent: Jun. 1, 1999

[54] APPARATUS FOR NON-INVASIVE MEASUREMENT WITHIN A HUMAN OR ANIMAL BODY

[75] Inventor: Ian Philip West, Cardiff, United Kingdom

[73] Assignee: Critikon Company, L.L.C., Tampa, Fla.

[21] Appl. No.: 08/681,590

[22] Filed: Jul. 29, 1996

[30] Foreign Application Priority Data

Jul. 31, 1995 [GB] United Kingdom ................... 9515648

[51] Int. Cl.⁶ ........................................................ A61B 5/00
[52] U.S. Cl. .......................................... 600/310; 600/323
[58] Field of Search ...................... 128/633, 664, 128/665; 600/310, 316, 322, 323, 324, 326, 340, 344, 473, 476

[56] References Cited

U.S. PATENT DOCUMENTS

| | | | |
|---|---|---|---|
| 5,419,321 | 5/1995 | Evans | 128/633 |
| 5,513,642 | 5/1996 | Ostrander | 128/633 |
| 5,522,388 | 6/1996 | Ishikawa et al. | 128/633 |
| 5,551,422 | 9/1996 | Simonsen et al. | 128/633 |

FOREIGN PATENT DOCUMENTS

| | | |
|---|---|---|
| 0 135 840 | 8/1984 | European Pat. Off. . |
| WO 93/11701 | 6/1993 | WIPO . |
| WO 94/12096 | 6/1994 | WIPO . |
| WO 94/27493 | 12/1994 | WIPO . |

*Primary Examiner*—Cary E. O'Connor
*Assistant Examiner*—Eric F. Winakur
*Attorney, Agent, or Firm*—Larry L. Saret; Laff, Whitesel, Conte & Saret, Ltd.

[57] ABSTRACT

An apparatus for non-invasive measurement within a human or animal body with an emitter for emitting electromagnetic radiation into the human or animal body and a detector for detecting the scattered and attenuated radiation. The detector comprises a first principal detector and at least one second reference detector. The second detector is disposed a distance from the emitter which is less than the distance of the first principal detector from the emitter. The second detector is disposed on a line of radius from the emitter which forms an angle with the line of the radius from the emitter on which the first principal detector lies.

11 Claims, 4 Drawing Sheets

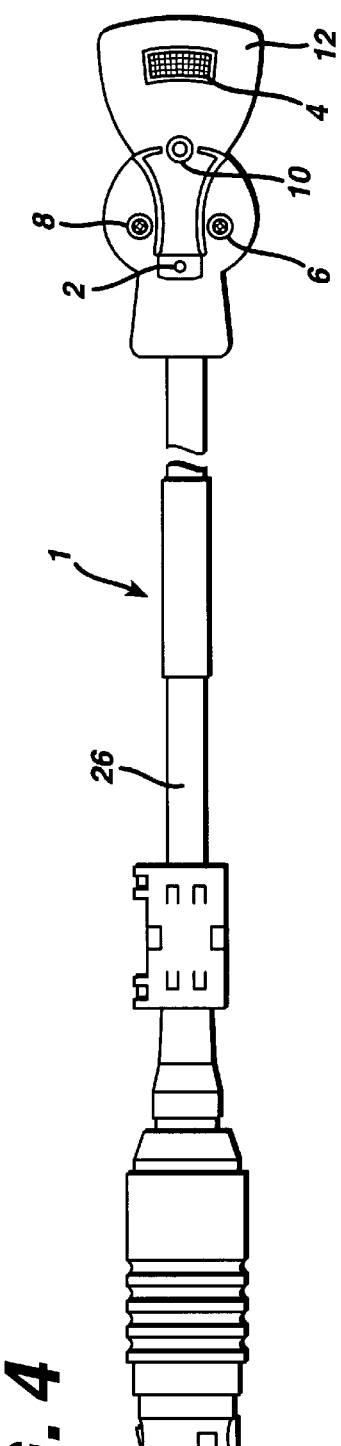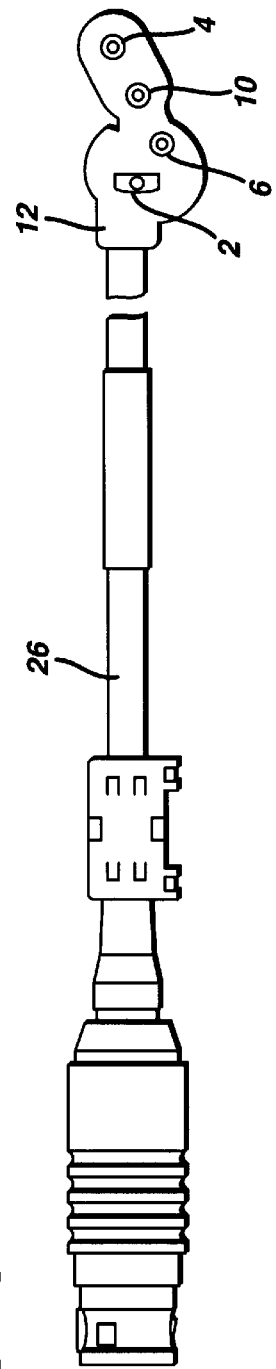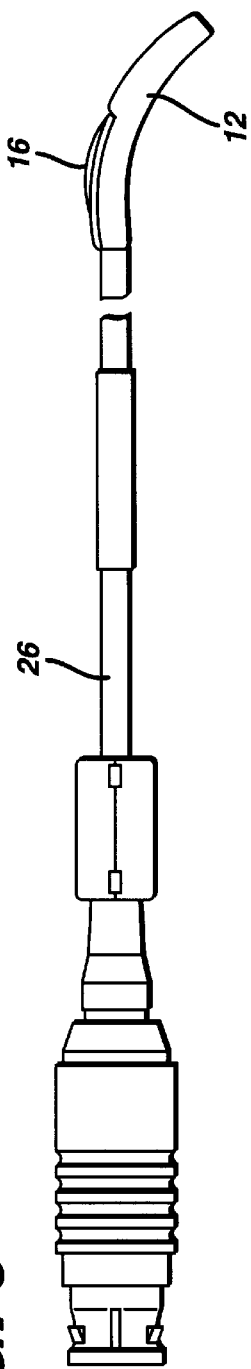

APPARATUS FOR NON-INVASIVE MEASUREMENT WITHIN A HUMAN OR ANIMAL BODY

This invention relates to an apparatus for non-invasive measurement within a human or animal body, in particular to an apparatus for such measurement utilising electromagnetic radiation.

Various forms of apparatus are known in which certain characteristics of tissue within a living body are measured by placing an electromagnetic radiation source adjacent the skin of the body and detecting the electromagnetic radiation received by one or more detectors positioned a predetermined distance away from the source. The characteristics that may be measured include tissue oxygenation.

U.S. Pat. No. 5,057,695 discloses a system for measuring the inside information of a substance with the use of light scattering, the system using more than one light source or detector with the source(s) and detector(s) placed in the same direction. WO 91/17697 describes a two channel detector system with the detectors arranged concentrically.

A point source of electromagnetic radiation emits equal radiation in all directions from the source. Known devices use a principal detector positioned a first distance away from the source which detects radiation which is scattered back to the detector having passed through the tissue being measured. Such known devices also include a second, reference detector placed between the source and the principal detector. As the distance between the second detector and the source is less than the distance between the source and the principal detector, the second detector detects light which has not penetrated as far into the tissue as the light reaching the principal detector. The signal from the second detector can be used to interpret the signal received from the principal detector to gain the maximum information regarding the tissue being measured.

For a minimum spatial requirement of the apparatus, the second detector is generally placed on the line of radius between the point source and the principal detector. This arrangement has the disadvantage of allowing only one second reference detector which may limit the performance of the system if there are localised inhomogeneities in the tissue close to the detector.

According to the present invention there is provided an apparatus for non-invasive measurement within a human or animal body comprising an emitter means for emitting electromagnetic radiation into the human or animal body, first radiation detection means spaced a first distance from the emitter means for detecting scattered radiation from within the human or animal body, and at least one second detection means disposed a distance from the emitter means which is less than the first distance, wherein the or each second detection means is disposed on a line of radius from the emitter means such that the or each line of radius on which a second detection means is disposed is at an angle to the line of radius on which the first detection means is disposed.

There may optimally be provided two second detection means unless the apparatus is for use as a neonatal sensor wherein one second detection means is required. Preferably, the angle between each line of radius on which a second detection means is disposed and the line of radius on which the first detection means is disposed is greater than 45 degrees. Preferably, the angle is 46 degrees.

The emitter means may emit electromagnetic radiation at at least two different wavelengths. A minimum of two distinct wavelengths are required to measure two parameters. More parameters can be measured by increasing the number of distinct wavelengths used. The wavelengths may be between 650 nm and 950 nm for detection of tissue oxygenation.

The first detection means may be of an arcuate form with a radius of curvature equal to the first distance. The first distance may optimally be between 40 and 50 millimetres, preferably 45 millimetres.

A light emitting diode may be disposed equidistant between the first detection means and each of the second detection means to calibrate the relative gains of the first and second detection means.

Optimally, the distance between the emitter means and each of the second detection means is in the range 10 to 20 millimetres preferably, 13 millimetres.

More than one first detection means may be distributed along an arc centred at the emitter means.

According to the second aspect of the present invention there is provided an apparatus for non-invasive measurement within a human or animal body comprising a housing with a first recess in which an emitter means is disposed, the emitter means being capable of emitting electromagnetic radiation, and at least two further recesses in which detection means are disposed for detecting radiation, the recesses having windows through which the radiation is emitted and detected, wherein the housing has a protective flap for enclosing the emitter means.

Preferably, the protective flap of the housing locks an end of a cable connected to the emitter means within the housing.

More than one detection means may be provided each with a window in the housing. A further recess may be provided for a light emitting diode. Preferably, apertures for the windows in the housing are tapered to allow maximum input and output of radiation.

Preferably, the housing is formed of a flexible, conformal material which is suitable for prolonged skin contact, the housing being pigmented black and moulded as one piece.

Preferably, the protective flap extends from one end of the housing with a hinge member joining a main body of the housing to the protective flap. The protective flap may carry positive locking means which co-operates with a corresponding locking means on the main body of the housing.

Embodiment of the present invention will now be described, by way of example only, with reference to the accompanying drawings in which:

FIG. 4 is a plan view of a connector and housing of the apparatus of the first embodiment;

FIG. 5 is a plan view of a connector and housing of an apparatus in accordance with a second embodiment of the invention;

FIG. 6 is a side view of the connector and housing of FIG. 5;

Figure 1:
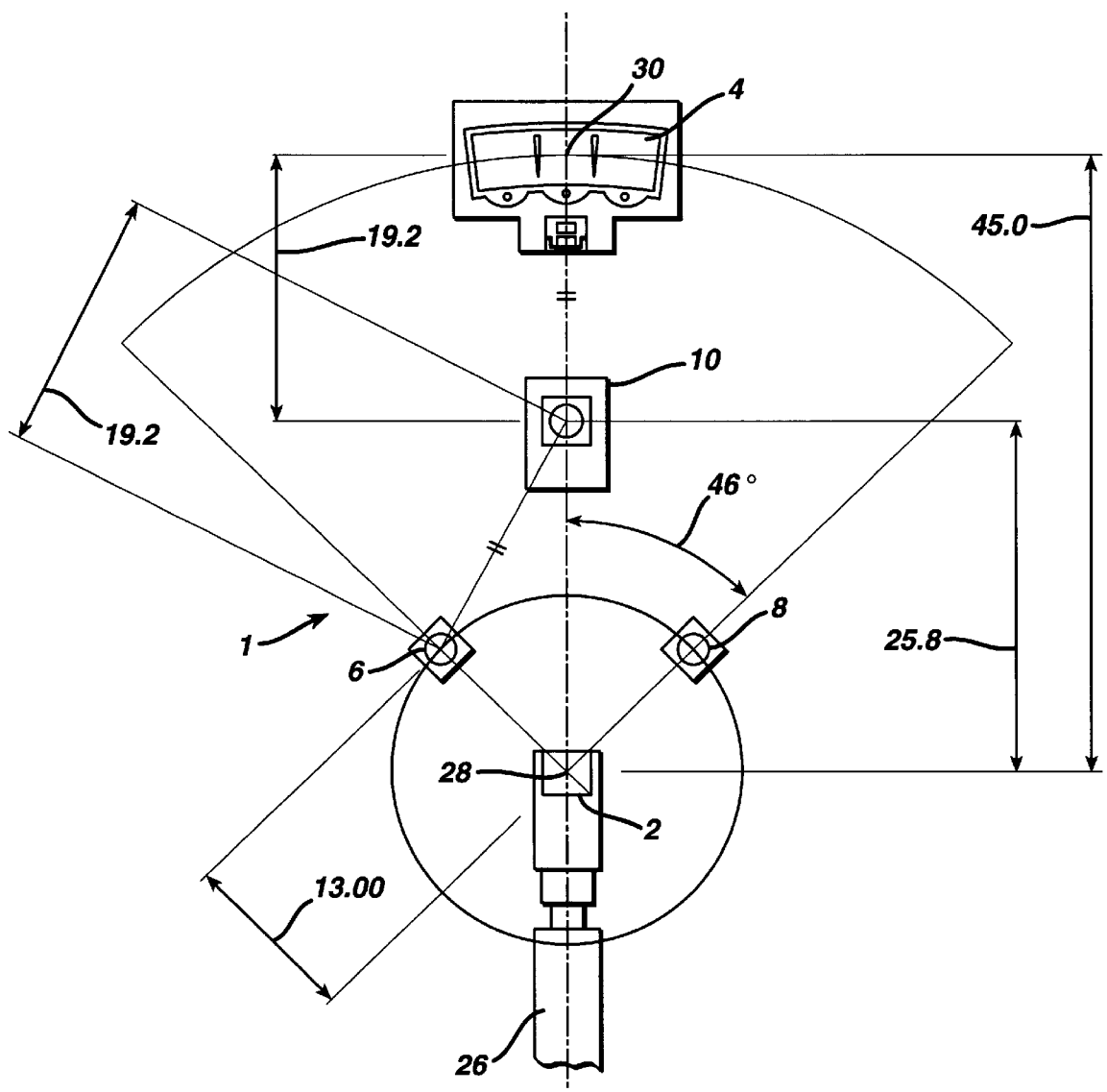
FIG. 1 is a schematic configuration of the surface contacting components of a first embodiment of the apparatus in accordance with the present invention.
Figure 2:
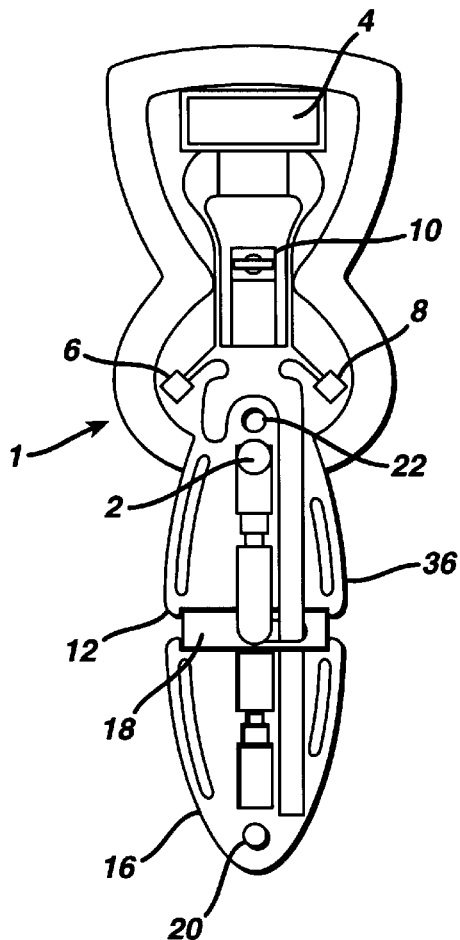
FIG. 2 is a plan view of a housing for the surface contacting components of the apparatus of the first embodiment of the present invention.
Figure 3:
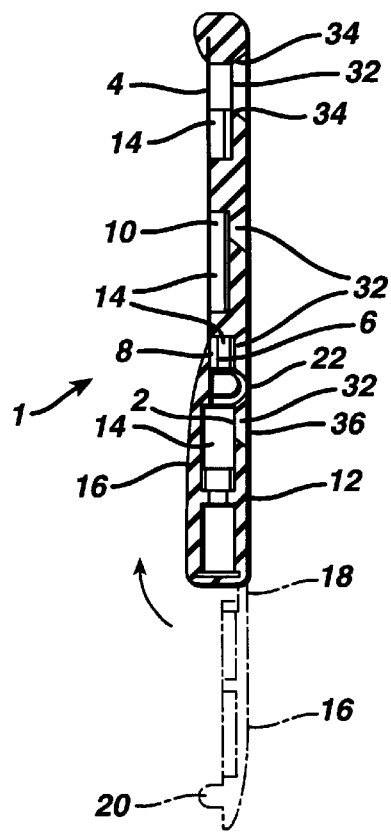
FIG. 3 is a cross-section through the embodiment of FIG. 2 with a protective flap shown in both an open and closed position.
Figure 7:
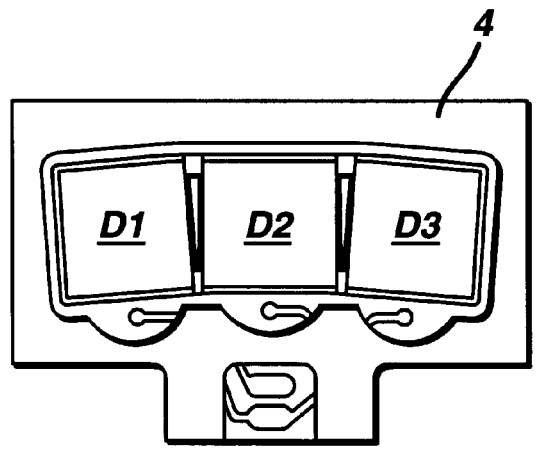
FIG. 7 is a front view of an arcuate photodetector used in the apparatus of the present invention.
Figure 8:
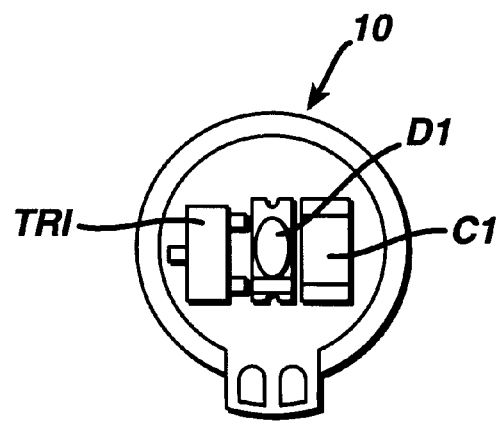
FIG. 8 is a front view of a light emitting diode used in the apparatus of the present invention.

Referring to FIGS. 1 to 4, a first embodiment of the apparatus is provided in the form of an adult system. The apparatus for non-invasive measurement within a human or animal body has an emitter means 2 for emitting electromagnetic radiation at four distinct wavelengths between the wavelengths of 650 nm and 950 nm. The electromagnetic radiation is transmitted to the emitter means 2 via an optical fibre cable 26. The emitter means 2 provides a point source of radiation from which radial lines can be extended such that the light reaching points on different lines of radius the same distance from the source is of the same intensity. A principal detector 4 has an arcuate form with a radius of 45 millimetres with the centre at the point source 28 of the emitter means 2.

A safety surface sensor device can be provided to ensure that the emitter means 2 only operates when the apparatus is in a desired position in relation to the tissue to be measured.

Two second detectors 6, 8 act as reference detectors to facilitate absolute quantification of the signal received by the principal detector 4. Each of the second detectors 6, 8 is disposed on a line of radius of a circle with its centre at the point source 28. Each of the lines of radius on which the second detectors 6, 8 are disposed forms an angle of 46 degrees with the line of radius which extends to a central point 30 of the principal detector 4. The two second detectors 6, 8 are placed a distance of 13 millimetres away from the point source 28.

A light emitting diode 10 is disposed equidistant from the principal detector 4 and the two second detectors 6, 8. The distance between the light emitting diode 10 and the detectors 4, 6, 8 is 19.2 millimetres.

The detectors 4, 6, 8 are formed of photodiode modules mounted onto a printed circuit board which is laminated to a frame. The whole assembly is wrapped in a metallic screen which protects against radio frequency interference which could cause noise on the signal. The screen has a mesh at the front so that light can reach the photodiode and a window glass is mounted on top of the mesh.

The principal detector 4 is made up of three photodiodes wired in parallel and mounted in an arc of radius corresponding to the distance to the emitter means 2.

The light emitting diode 10 is also mounted on a printed circuit board which sits inside a frame. As with the photodiodes, a screen is wrapped around the frame, in this case to prevent radio frequency emissions which might cause noise on the photodetector signals. A window glass is mounted on top of the aperture in the screen in front of the light emitting diode 10.

An apparatus for providing non-invasive measurement can be adapted to a neonatal device by reducing the size of the apparatus by using a single, second reference detector. The single reference detector can be placed at a 46 degree angle to a principal detector as with the larger model. A second embodiment of the apparatus 1 is shown in FIG. 4 and 5 designed for neonatal use with only one secondary detector 6. The distances from the emitter means 2 to the principal detector 4 and the secondary detector are 35 mm and 10 mm respectively.

FIGS. 4 and 5 show the connector for attachment to the unit containing the laser sources and the operating instrumentation.

The surface contacting components of both the first and second embodiments of the apparatus 1 are remote from a unit containing the laser sources and operating instrumentation. The unit is attached to the surface contacting components via a mixed fibre optic/electrical connector. The connector and the integral fibre optic cable 26 are designed to minimise noise and crosstalk in order to optimise sensor performance.

The connector enables the laser sources to be housed remotely from the emitter means 2 and pulsed laser radiation is transmitted to the emitter means 2 via fibre optics 26. The light emitting diode 10 is powered and controlled by a pulse signal from circuitry in the unit. The signals received by the detectors 4, 6, 8 are conducted via twisted screen wires in the cable 26 and screened contacts in the connector to low noise amplifier circuitry in the unit.

A housing 12 is provided in which the surface contacting components of both embodiments of the apparatus 1 are encased. The housing 12 is connected to the laser sources and operating electronics in the unit via the mixed electrical/fibre optic connector. The housing 12 has a number of recesses 14 in which the skin contacting components in the form of the emitter means 2, the detectors 4, 6, 8, and the light emitting diode 10 are housed. Each of the recesses 14 has a window aperture 32, each aperture 32 having chamfered edges 34 which taper away from the components. The window apertures 32 are placed adjacent the skin of the human or animal body being measured. The housing 12 may be fixed to the body by fixation means or adhesion means ensuring that the only light paths between emitter means 2 and detectors 4, 6, 8 are through the tissue under investigation.

The housing 12 of the second embodiment is moulded with a pre-formed radius of curvature of approximately 45 mm to make it easier to fit to a small neonate's head.

The housing 12 has a flap portion 16 extending from a first end of the housing 12. The flap portion 16 is attached to the main body 36 of the housing 12 by a hinge 18. The flap portion 16 is closable over the emitter means 2 and secures the optical fibre cable 26 which transmits light to the emitter means 2. The flap portion 16 has securement means in the form of a male portion 20 extending from the flap portion 16 with a corresponding female portion 22 on the main body 36 of the housing 12.

The housing 12 is formed of a flexible conformal material which maintains the form of the surface to which it is applied and which is suitable for prolonged skin contact. The material is resistant to chemical degradation so that the sensor housing 12 can be cleaned by an approved method before use. The housing 12 is moulded as one piece with material removed from recessed areas to increase the flexibility of the housing 12. The material is silicone or a similar biocompatible elastomer. The housing 12 is pigmented black and is strongly absorbing to visible and near infrared radiation.

In use of the apparatus of the first embodiment, electromagnetic radiation at four distinct wavelengths is emitted by the emitter means 2 and extends outwardly from the point source 28 of the emitter means 2 into the skin and tissue of the human or animal body being measured. The four wavelengths are used to measure three parameters. Three wavelengths could be used but a fourth wavelength improves the accuracy of the measurement. The electromagnetic radiation is scattered by the tissue within the human or animal body and some of the scattered radiation is detected by the principal detector 4 and the two second reference detectors 6, 8. The radiation reaching the principal detector 4 has passed through deeper tissue than the radiation reaching the two secondary reference detectors 6, 8. As the signal reaching the principal detector 4 is weaker than the signal reaching the two secondary reference detectors 6, 8 the amplification gain of the principal detector 4 must be greater than that of the two secondary reference detectors 6, 8.

The total detector area of the principal detector 4 is larger than that of the secondary detectors 6, 8 so as to increase the signal level received. Using a larger detector area improves the signal to noise ratio of the apparatus, but detector area must be balanced by the need to maintain a measurement with good spatial resolution. Good spatial resolution is maintained by distributing the detector area along the radius of curvature of an arc centred at the emitter means 2 and not along the line towards or away from the emitter means 2.

The arcuate form of the principal detector 4 receives as much scattered radiation as possible at a given distance from the point source 28. For maximum spatial resolution of the tissues under investigation the width of all the detectors 4, 6, 8 in the direction of the source should be narrow as possible. The sensitivity is increased by increasing the elongation of the detectors 4, 6, 8 along an arc with a centre of curvature of the point of the light source whilst keeping within the limits of the physical size of the sensor.

The two secondary reference detectors 6, 8 are disposed at separate points on a circle with its centre at the emitter means 2 to provide two separate references. Having two detectors means that the individual detector areas are small, i.e. narrow along the radius of the circle on which they are disposed. This improves the spatial resolution of the measurement. In the neonatal apparatus, as described in the second embodiment, two secondary reference detectors 6, 8 are not required as the light absorption by the tissue is less and the emitter/detector spacing is less so that the signal level is higher. Otherwise, the operation of the apparatus of the second embodiment is the same as the first embodiment.

In order to ensure that the relative gains of the detectors 4, 6, 8 are known and in order to take into consideration coupling variations and differences in pigmentation of local tissue, a light emitting diode 10 is place equidistant between the detectors 4, 6, 8. The light emitting diode 10 emits electromagnetic radiation at a further wavelength of approximately 830 nm, which is mid-way between and distinct from the wavelength of the lasers of the emitter means 2. The radiation from the light emitting diode 10 is received by the principal detector 4 and the reference detectors 6, 8. The mathematical ratio of the radiation signals of the light emitting diode 10 received at the principal 4 and secondary 6, 8 detectors is used to normalise the laser radiation signals of the emitter means 2 received at the detectors 4, 6, 8. The normalised signals are then used in an algorithm to calculate the tissue oxygenation.

The principle of the technique of using a light emitting diode 10 assumes that the light paths of the radiation from the light emitting diode 10 and the emitter means 2 through the superficial or surface tissues are the same immediately beneath the detectors 4, 6, 8. Therefore, if there is a freckle or a bead of moisture underneath one detector 4, 6, 8, this will affect radiation from both the light emitting diode 10 and the emitter means 2 and the effect of the abberation will be cancelled.

If there is something which affects the radiation path of the light emitting diode 10 but not the emitter means 2, for example a large superficial blood vessel which is close to, but not directly beneath the detector 4, 6, 8, then this would cause an error in the measurement. If two reference secondary detectors 6, 8 are provided which are sufficiently spaced apart, the effect of the error would be reduced because of averaging assuming that both secondary detectors 6, 8 are not subject to the source of error.

It has been found that a balance must be maintained between placing the principal detector 4 as far away from the emitter means 2 as possible to pick up radiation scattered from deeper tissue whilst minimising the apparatus size.

By using one or more reference detectors 6, 8 to subtract the unwanted signals from the superficial or surface tissues, the principal detector 4 can be nearer the emitter means 2 than it would otherwise be able to be.

The secondary detectors 6, 8 must have a channel that can receive very high intensity laser signals from the emitter means 2 and very low intensity signals from the light emitting diode 10. In order that the amplifier is not saturated by the laser signals, the gain is much lower than that for the principal detector 4. This results in comparatively low level signals from the light emitting diode 10 and therefore it is important that the level of noise and offsets is also low in order to maintain accuracy.

In the case of the channel of the principal detector 4, the signals from the light emitting diode 10 are higher than the laser signals, but they are more closely matched than for the channel of the secondary detectors 6, 8.

The tissue has a characteristic absorption at the electromagnetic radiation wavelengths which have passed through it, therefore details of the tissue can be deduced by processing the received light intensity signals using an appropriate algorithm.

Modifications and improvements can be made to the aforesaid without departing from the scope of the present invention.

I claim:

1. An apparatus for non-invasive measurement within a human or animal body comprising an emitter means for emitting electromagnetic radiation into the human or animal body, first radiation detection means spaced a first distance from the emitter means for detecting scattered radiation from within the human or animal body, said first radiation detection means being of an arcuate form with a radius of curvature equal to the first distance, and at least one second detection means disposed a distance from the emitter means which is less than the first distance for detecting scattered radiation, wherein said at least one second detection means is disposed at a discrete location on a line of radius along a surface from the emitter means such that the line of radius on which a second detection means is disposed is at an angle to the line of radius on which the first detection means is disposed.

2. An apparatus as claimed in claim 1, wherein there are two second detection means.

3. An apparatus as claimed in claim 1, wherein the angle between each line of radius on which a second detection means is disposed and the line of radius on which the first detection means is disposed is greater than 45 degrees.

4. An apparatus as claimed in claim 3, wherein the angle is 46°.

5. An apparatus as claimed in claim 1, wherein the emitter means emits electromagnetic radiation at at least two different wavelengths.

6. An apparatus as claimed in claim 1, wherein the emitter means emits electromagnetic radiation at wavelengths between approximately 650 nm and 950 nm.

7. An apparatus as claimed in claim 1, wherein the first distance is between 40 and 50 millimetres.

8. An apparatus as claimed in claim 1, wherein a light emitting diode is disposed equidistant between the first detection means and each of the second detection means.

9. An apparatus as claimed in claim 1, wherein the distance between the emitter means and each of the second detection means is in the range 10 to 20 millimetres.

10. An apparatus as claimed in claim 1, wherein there is more than one first detection means distributed along an arc centred at the emitter means.

11. An apparatus for non-invasive measurement within a human or animal body comprising an emitter means for emitting electromagnetic radiation into the human or animal body, first radiation detection means spaced a first distance from the emitter means from 40 millimeters to 50 millimeters for detecting scattered radiation from within the human or animal body, and at least one second detection means disposed a distance from the emitter means which is less than the first distance for detecting scattered radiation, wherein said at least one second detection means is disposed at a discrete location on a line of radius along a surface from the emitter means such that the line of radius on which a second detection means is disposed is at an angle to the line of radius on which the first detection means is disposed.

* * * * *